United States Patent [19]

Ecker

[11] Patent Number: 5,166,195
[45] Date of Patent: Nov. 24, 1992

[54] ANTISENSE INHIBITORS OF THE HUMAN IMMUNODEFICIENCY VIRUS PHOSPHOROTHIOATE OLIGONUCLEOTIDES

[75] Inventor: David J. Ecker, Carlsbad, Calif.
[73] Assignee: ISIS Pharmaceuticals, Inc., Carlsbad, Calif.
[21] Appl. No.: 521,907
[22] Filed: May 11, 1990
[51] Int. Cl.$^5$ .............................................. A61K 31/70
[52] U.S. Cl. ...................................... 514/44; 536/27; 536/28; 536/29
[58] Field of Search ................. 536/27, 28, 29; 514/44

[56] References Cited

U.S. PATENT DOCUMENTS 4,959,463 9/1990 Froehler et al. ....................... 536/27

OTHER PUBLICATIONS

S. Argawal, J. Goodchild, M. P. Civeira, A. H. Thornton, P. S. Sarin, P. C. Zamecnik, *Proc. Nat'l Acad. Sci.* USA 85, 7079 (1988).
S. Agarwal, T. Ikeuchi, D. Sun, P. S. Sarin, A. Konopka, J. Maizel, *Proc. Nat'l Acad. Sci.* USA 86, 7790 (1989).
B. Berkhout, *Cell* 59, 273 (1989).
H. M. Buck, L. H. Koole, M. H. P. van Gendersen, L. Smith, J. L. M. C. Green, S. Jurriaans and J. Goudsmit. *Science* 248, 208–212 (1990).
S. Feng, E. C. Holland, *Nature* 334, 165 (1988).
J. A. Garcia, D. Harrich, E. Soultanakis, F. Wu, R. Mitsuyasu, R. B. Gaynor, *EMBO J.* 8, 765 (1989).
J. Goodchild, S. Agrawal, M. P. Civeira, P. S. Sarin, D. Sun, P. C. Zamecnik, *Proc. Nat'l. Acad. Sci.* USA 85, 5507 (1988).
W. A. Haseltine, F. Wong-Staal, Scientific American Oct., 52 (1988).
P. Henthorn, P. Zervos, M. Raducha, H. Harris, T. Kadesch, *Proc. Nat'l. Acad. Sci.* USA 85, 6342 (1988).
Michael F. Laspia, Andrew, P. Rice, Michael, B. Matthews, *Cell* 59, 283 (1989).
R. L. Letsinger, G. R. Zhang, D. K. Sun, T. Ikeuchi, P. S. Sarin, *Proc. Nat'l. Acad. Sci.* USA 86, 6553 (1989).
D. S. Loose-Mitchell, TIPS, vol. 9, pp. 45–47 (1988).
C. J. Marcus-Sekura, *Anal. Biochemistry*, vol. 172, 289–295 (1988).
M. Matsukura, K. Shinozuka, G. Zon, et al. *Proc. Natl. Acad. Sci.* USA 84, 7706 (1987).
K. Mori, C. Boiziau, C. Cazenave, et al., *Nucleic Acids Res.* 17, 8207 (1989).
P. S. Sarin, S. Agrawal, M. P. Civeira, J. Goodchild, T. Ikeuchi, P. C. Zamecnik, *Proc. Nat'l. Acad. Sci.* USA 85, 7448 (1988).
Philip, A. Sharp, Robert, A. Marciniak, *Cell* 59, 229 (1989).
S. Shibahara, S. Mukai, H. Morisawa, H. Nakashima, S. Kobayashi, N. Yamamoto, *Nucl. Acids Res.* 17, 239 (1989).
C. A. Stein & J. S. Cohen, *Cancer Research*, vol. 48, pp. 2659–2668 (1988).
M. Stevenson, P. L. Iversen, *J. Gen. Virol.* 70, 2673 (1989).
A. R. Van der Krol, J. N. Mol, & A. R. Stuitje, *BioTechniques*, vol. 6, pp. 958–973 (1988).
J. Walder, *Genes & Development*, vol. 2, pp. 502–504 (1988).
J. A. Zaia, J. J. Rossi, G. J. Murakawa, P. A. Spallone, D. A. Stephens, B. E. Kaplan, *J. Virol*, 62, 3914 (1988).
G. Zon, *Pharmaceutical Research*, vol. 5, pp. 539–549 (1988).
P. C. Zamecnik, J. Goodchild, Y. Taguchi, P. S. Sarin, *Proc. Nat'l. Acad. Sci.* USA 83, 4143 (1986).
G. Zon, *Journal of Protein Chemistry*, vol. 6, pp. 131–145 (1987).

Primary Examiner—Johnnie R. Brown
Assistant Examiner—L. Eric Crane
Attorney, Agent, or Firm—Woodcock Washburn Kurtz Mackiewicz & Norris

[57] ABSTRACT

Methods for modulating the expression of the HIV tat gene are disclosed comprising contacting tat RNA with oligonucleotide or oligonucleotide analog which can bind with at least a portions of the RNA. In accordance with the preferred embodiments, oligonucleotides or oligonucleotide analogs are designed to bind to portions of the tat RNA which are of significance to the expression of the gene coding for said RNA. In accordance with a preferred embodiment, methods of treatment of human immunodeficiency virus are disclosed.

2 Claims, 3 Drawing Sheets

```
   1 GGGUCUCUCU GGUUAGACCA GAUCUGAGCC UGGGAGCUCU CUGGCUAACU
  51 AGGGAACCCA CUGCUUAAGC CUCAAUAAAG CUUGCCUUGA GUGCUUCAAG
 101 UAGUGUGUGC CCGUCUGUUG UGUGACUCUG GUAACUAGAG AUCCCUCAGA
 151 CCCUUUUAGU CAGUGUGGAA AAUCUCUAGC AGUGGCGCCC GAACAGGGAC
 201 CUGAAAGCGA AAGGGAAACC AGAGCUCUCU CGACGCAGGA CUCGGCUUGC
 251 UGAAGCGCCC GCACGGCAAG AGGCGAGGGG CGGCGACUGA AUGGGUGUC
 301 GACAUAGCAG AAUAGGCGUU ACUCGACAGA GGAGAGCAAG AAAUGGAGCC
 351 AGUAGAUCCU AGACUAGAGC CCUGGAAGCA UCCAGGAAGU CAGCCUAAAA
 401 CUGCUUGUAC CAAUUGCUAU UGUAAAAAGU GUUGCUUUCA UUGCCAAGUU
 451 UGUUUCAUAA CAAAAGCCUU AGGCAUCUCC UAUGGCAGGA AGAAGCGGAG
 501 ACAGCGACGA AGACCUCCUC AAGGCAGUCA GACUCAUCAA GUUUCUCUAU
 551 CAAAGCAACC CACCUCCCAA UCCCGAGGGG ACCCGACAGG CCCGAAGGAA
 601 UAGAAGAAGA AGGUGGAGAG AGAGACAGAG ACAGAUCCAU UCGAUUAGUG
 651 AACGGAUCCU UAGCACUUAU CUGGGACGAU CUGCGGAGCC UGUGCCUCUU
 701 CAGCUACCAC CGCUUGAGAG ACUUACUCUU GAUUGUAACG AGGAUUGUGG
 751 AACUUCUGGG ACGCAGGGGG UGGGAAGCCC UCAAAUAUUG GUGGAAUCUC
 801 CUACAGUAUU GGAGUCAGGA GCUAAAGAAU AGUGCUGUUA GCUUGCUCAA
 851 UGCCACAGCU AUAGCAGUAG CUGAGGGGAC AGAUAGGGUU AUAGAAGUAG
 901 UACAAGGAGC UUAUAGAGCU AUUCGCCACA UACCUAGAAG AAUAAGACAG
 951 GGCUUGGAAA GGAUUUUGCU AUAAGAUGGG UGGCAAGUGG UCAAAAAGUA
1001 GUGUGGUUGG AUGGCCUGCU GUAAGGGAAA GAAUGAGACG AGCUGAGCCA
1051 GCAGCAGAUG GGUGGGAGC AGCAUCUCGA GACCUAGAAA AACAUGGAGC
1101 AAUCACAAGU AGCAACACAG CAGCUAACAA UGCUGAUUGU GCCUGGCUAG
1151 AAGCACAAGA GGAGGAGGAG GUGGGUUUUC CAGUCACACC UCAGGUACCU
1201 UUAAGACCAA UGACUUACAA GGCAGCUGUA GAUCUUAGCC ACUUUUUAAA
1251 AGAAAAGGGG GGACUGGAAG GGCUAAUUCA CUCCCAACGA AGACAAGAUA
```

*Fig. 1A*

```
1301 UCCUUGAUCU GUGGAUCUAC CACACACAAG GCUACUUCCC UGAUUAGCAG
1351 AACUACACAC CAGGGCCAGG GAUCAGAUAU CCACUGACCU UUGGAUGGUG
1401 CUACAAGCUA GUACCAGUUG AGCCAGAGAA GUUAGAAGAA GCCAACAAAG
1451 GAGAGAACAC CAGCUUGUUA CACCCUGUGA GCCUGCAUGG AAUGGAUGAC
1501 CCGGAGAGAG AAGUGUUAGA GUGGAGGUUU GACAGCCGCC UAGCAUUUCA
1551 UCACAUGGCC CGAGAGCUGC AUCCGGAGUA CUUCAAGAAC UGCUGACAUC
1601 GAGCUUGCUA CAAGGGACUU UCCGCUGGGG ACUUUCCAGG GAGGCGUGGC
1651 CUGGGCGGGA CUGGGGAGUG GCGAGCCCUC AGAUCCUGCA UAUAAGCAGC
1701 UGCUUUUUGC CUGUACUGGG UCUCUCUGGU UAGACCAGAU CUGAGCCUGG
1751 GAGCUCUCUG GCUAACUAAG GAACCCACUG CUUAAGCCUC AAUAAAGCUU
1801  GCCUUGAGUG CUGUCAAAAA AAAAAAAAAA AAA
```

*Fig. 1B*

ANTISENSE INHIBITORS OF THE HUMAN IMMUNODEFICIENCY VIRUS PHOSPHOROTHIOATE OLIGONUCLEOTIDES

FIELD OF THE INVENTION

This invention relates to the field of therapeutics, particularly the treatment of infections of the human immunodeficiency virus (HIV). It relates to the design, synthesis and application of oligonucleotides and oligonucleotide analogs which inhibit the activity of the HIV and other retroviruses.

BACKGROUND OF THE INVENTION

This invention relates to materials and methods for modulating the activity of HIV RNA. The invention generally relates to the field of "antisense" compounds, compounds which are capable of specific hybridization with a nucleotide sequence of an RNA. In accordance with preferred embodiments, this invention is directed to methods for achieving therapeutic treatment of disease and regulating gene expression in experimental systems.

It is well known that most of the bodily states in mammals including infectious disease states, are effected by proteins. Such proteins, either acting directly or through their enzymatic functions, contribute in major proportion to many diseases in animals and man. Classical therapeutics has generally focused upon interactions with such proteins in efforts to moderate their disease causing or disease potentiating functions. Recently, however, attempts have been made to moderate the actual production of such proteins by interactions with molecules that direct their synthesis, intracellular RNA. By interfering with the production of proteins, it has been hoped to effect therapeutic results with maximum effect and minimal side effects. It is the general object of such therapeutic approaches to interfere with or otherwise modulate gene expression leading to undesired protein formation.

One method for inhibiting specific gene expression which has been adopted to some degree is the "antisense" approach, where oligonucleotide analogs complimentary to a specific, target, messenger RNA, mRNA sequence are used. A number of workers have reported such attempts. Pertinent reviews include C. A. Stein & J. S. Cohen, *Cancer Research*, vol. 48, pp. 2659-2668 (1988); J. Walder, *Genes & Development*, vol. 2, pp. 502-504 (1988); C. J. Marcus-Sekura, *Anal. Biochemistry*, vol 172, 289-295 (1988); G. Zon, *Journal of Protein Chemistry*, vol. 6, pp-131-145 (1987); G. Zon, *Pharmaceutical Research*, vol. 5, pp. 539-549 (1988); A. R. Van der Krol, J. N. Mol, & A. R. Stuitje, *BioTechniques.*, vol. 6, pp. 958-973 (1988) and D. S. Loose-Mitchell, *TIPS*, vol. 9, pp. 45-47 (1988). Each of the foregoing provide background concerning general antisense theory and prior techniques.

Prior attempts to inhibit HIV by various antisense approaches have been made by a number of researchers. Zamecnic and coworkers have used phosphodiester oligonucleotides targeted to the reverse transcriptase primer site and to splice donor/acceptor sites P. C. Zamecnik, J. Goodchil Taguchi, P. S. Sarin, *Proc. Natl. Acad. Sci. USA* 83, 4143 (1986). Goodchild and coworkers have made phosphodiester compounds targeted to the initiation sites for translation, the cap site, the polyadenylation signal, the 5' repeat region and a site between the gag and pol genes. J. Goodchild, S. Agrawal, M. P. Civeira, P. S. Sarin, D. Sun, P. C. Zamecnik, *Proc. Natl. Acad. Sci. U.S.A.* 85, 5507 (1988). In the Goodchild study, the greatest activity was achieved by targeting the polyadenylation signal. Agrawal and coworkers have extended the studies of Goodchild by using chemically modified oligonucleotide analogs which were also targeted to the cap and splice donor/acceptor sites. S. Agarwal, J. Goodchild, M.P. Civeira, A. H. Thornton, P. S. Sarin, P. C. Zamecnik, *Proc. Nat'l. Acad. Sci. USA* 85, 7079 (1988). A portion of one of these overlapped a portion of the HIV TAR region but was not found to have exemplary effect. Neither was this oligonucleotide analog designed to interfere with the HIV TAR region. Agrawal and coworkers have used oligo-nucleotide analogs targeted to the splice donor/acceptor site inhibit HIV infection in early infected and chronically infected cells. S. Agrawal, T. Ikeuchi, D. Sun, P. S. Sarin, A. Konopka, J. Maizel, *Proc. Natl. Acad. Sci. U. S. A.* 86, 7790 (1989).

Sarin and coworkers have also used chemically modified oligonucleotide analogs targeted to the cap and splice donor/acceptor sites. P. S. Sarin, S. Agrawal, M. P. Civeira, J. Goodchild, T. Ikeuchi, P. C. Zamecnik, *Proc. Natl. Acad. Sci. U. S. A.* 85, 7448 (1988). Zia and coworkers have also used an oligonucleotide analog targeted to a splice acceptor site to inhibit HIV. J. A. Zaia, J. J. Rossi, G. J. Murakawa, P. A. Spallone, D. A. Stephens, B. E. Kaplan, *J. Virol.* 62, 3914 (1988). Matsukura and coworkers have synthesized oligonucleotide analogs targeted to the initiation of translation of the rev gene mRNA. M. Matsukura, K. Shinozuka, G. Zon, et al, *Proc. Natl. Acad. Sci. USA* 84, 7706 (1987); R. L. Letsinger, G. R. Zhang, D. K. Sun, T. Ikeuchi, P. S. Sarin, *Proc. Natl. Acad. Sci. U. S. A.* 86, 6553 (1989). Mori and coworkers have used a different oligonucleotide analog targeted to the same region as Matsukura. K. Mori, C. Boiziau, C. Cazenave, et al, Nucleic Acads Res. 17, 8207 (1989). Shibahara and coworkers have used oligonucleotide analogs targeted to a splice acceptor site as well as the reverse transcriptase primer binding site. S. Shibahara, S. Mukai, H. Morisawa, H. Nakashima, S. Kobayashi, N. Yamamoto, *Nucl. Acids Res.* 17, 239 (1989). Letsinger and coworkers have synthesized and tested a oligonucleotide analogs with conjugated cholesterol targeted to a splice site. K. Mori, C. Boiziau, C. Cazenave, et al, *Nucleic Acids Res.* 17, 8207 (1989). Stevenson and Iversen have conjugated polylysine to oligonucleotide analogs targeted to the splice donor and the 5'-end of the first exon of the tat gene. M. Stevenson, P. L. Iversen, *J. Gen. Virol.* 70, 2673 (1989). Buck and coworkers have recently described the use of phosphate-methylated DNA oligonucleotides targeted to HIV mRNA and DNA. H. M. Buck, L. H. Koole, M. H. P. van Gendersen, L. Smith, J. L. M. C. Green, S. Jurriaans and J. Goudsmit. *Science* 248, 208-212 (1990).

These prior attempts at targeting HIV have largely focused on the nature of the chemical modification used in the oligonucleotide analog. Although each of the above publications have reported some degree of success in inhibiting some function of the virus, a general therapeutic scheme to target HIV and other retroviruses has not been found. Accordingly, there has been and continues to be a long-felt need for the design of oligonucleotides and oligonucleotide analogs which are capable of effective, therapeutic antisense use.

This long-felt need has not been satisfied by prior work in the field of antisense oligonucleotide therapy for HIV and other retroviruses and viruses. Others have failed to identify target sites in which antisense oligonucleotides or oligonucleotide analogs are therapeutically effective at reasonable rates of application.

OBJECTS OF THE INVENTION

It is a principal object of the invention to provide therapies for human diseases, particularly the human immunodeficiency virus and other human retroviruses.

It is a further object of the invention to provide molecules, especially oligonucleotides and oligonucleotide analogs which perturb the structure of mRNA.

Yet another object of this invention is to modulate gene expression in cells.

A further object is to interfere with the secondary structure of RNAs through interaction of those structures with oligonucleotides or oligonucleotide analogs.

These and other objects of this invention will become apparent from a review of the instant specifications.

SUMMARY OF THE INVENTION

Prior attempts at antisense targeting to HIV have been focused on inhibition of the synthesis of some particular viral protein thought to be essential to the success of the infection. In the present invention, the same goal (inhibition of viral gene expression) is achieved, but greater, therapeutically significant activity is obtained by targeting particular sites on the HIV or other retrovirus RNA. In the present invention, target RNAs which have important biological function have been found to be the key target sites. It has been determined that targeting these RNA regions is a key to effective antisense therapy with oligonucleotides and oligonucleotide analogs.

It has now been discovered that compounds which specifically bind the tat RNA structure and interfere with tat trans-activation have activity as therapeutic agents for HIV infection. It is intended that all strains of HIV fall within the spirit and scope of this invention. While different strains of HIV may have different tat RNA sequences, this invention can be practiced on alternative strains of HIV by changing the sequence of the oligonucleotide or oligonucleotide analog to complement the structure of the alternative strain in accordance with the present teachings.

In accordance with the present invention, methods of modulating the expression of genes are provided. The targeted RNA, or cells containing it, is contacted with oligonucleotide or oligonucleotide analog which can bind with at least a portion of the RNA. The gene is generally one which is believed to give rise to a disease state in an organism and is typically a virus or, preferably, a retrovirus such as HIV, although other infectious organisms can be so attacked leading to therapeutic methods for treating diseased states by administering oligonucleotides or oligonucleotide analogs to animals suspected of having viral or retroviral infections.

It has now been found that oligonucleotide or oligonucleotide analogs can be designed, especially for retroviruses such as HIV, which are effective in diminishing the infection. For HIV, a number of sequences have been found which are effective and persons of ordinary skill in the art will likely identify others. These sequences are the first, practically effective antisense sequences which have been shown to be effective in inhibiting the tat region of HIV and to lead to HIV therapeutics. Accordingly, this invention provides oligonucleotides and oligonucleotide analogs capable of binding with at least a portion of tat mRNA of HIV. Such oligonucleotides and analogs have been found corresponding to the nucleotide sequences G G C T C C A T T T C T T G C T C T C , CCATTTCTTGCTCTCCTCTGT, GCTATGTCGACACCCAATTC, CCGCCCCTCGCCTCTTGCCG, CGGGTCCCCTCGGGATTGGG, and CACCTTCTTCTTCTATTCCT. It is preferred that the oligonucleotides and analogs have at least about 6 contiguous subunits of such sequences, with at least about 10 being preferred and at least about 15 being still more preferred. It is preferred for some embodiments that the oligonucleotide or oligonucleotide analog substantially correspond to a given sequence. By this is meant that the oligonucleotide or analog have every subunit of the sequence or an effective substitute. Thus, substitutions such as U for T and the like may be made in wild type oligonucleotides. Additionally, of course, other chemical modifications to form oligonucleotide analogs may be made without departing from the spirit of this invention.

The sequence portions may fall anywhere within the given sequences to likely have effect. Oligonucleotides and analogs, such as the preferred phosphorothioate analogs may be presented in a pharmaceutically acceptable carrier.

Methods of inhibiting gene expression, especially tat gene expression have also been discovered. Such inhibition may be employed for therapeutics, for diagnosis or for research. Thus, methods of treating an animal suspected of having a disease characterized by tat gene expression, especially AIDS, have been discovered comprising contacting the animal with oligonucleotides or oligonucleotide analogs in accordance with this invention.

It is preferred that the oligonucleotide or oligonucleotide analog be capable of binding with at least about six subunits of the RNA portion. It is more preferred that from eight to fifty units be capable of being bound, with from about 10 to about 20 subunits being even more preferred.

In accordance with preferred embodiments, the oligonucleotide of oligonucleotide analog is capable of forming a duplex structure with the portion of RNA. While the mechanism of the interaction is not known with certainty, it is possible that it may effect modulation of gene expression through a number of ways.

In accordance with preferred embodiments, the RNA portion which is interfered with comprises at least a part of the tat mRNA of HIV. The oligonucleotides and oligonucleotide analogs in accordance with this invention are, themselves believed to be novel. Thus, oligonucleotides which are capable of interacting with portions of tat RNA are comprehended. Thus, animals suspected of having the disease are contacted with oligonucleotide or oligonucleotide analog which can bind with the tat RNA. In particular, the present invention is believed to be effective in the treatment of HIV infections in mammals, especially man.

BRIEF DESCRIPTION OF THE DRAWINGS

FIGS. 1A and 1B depicts a linear HIV-1 tat mRNA sequence.

DETAILED DESCRIPTION OF PREFERRED EMBODIMENTS

Figure 2:
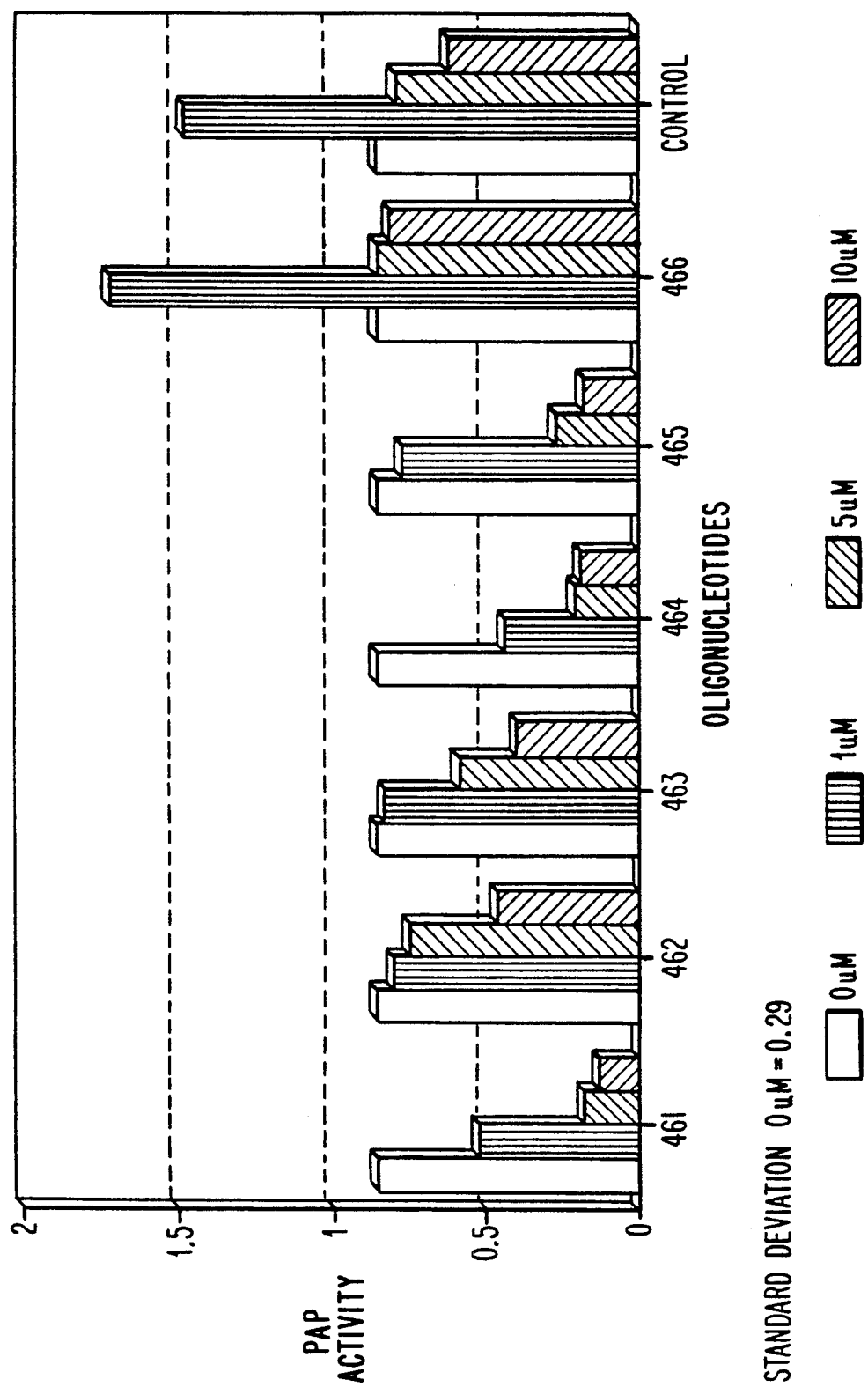
FIG. 2 depicts the activity of a series of oligonucleotides and oligonucleotide analogs in accordance with this invention in a cell culture assay for TAR/tat transactivation.

It has been discovered to be possible to regulate the activity of HIV tat RNA in cells by introducing oligonucleotides or oligonucleotide analogs which bind to the tat mRNA. The oligonucleotides or oligonucleotide analogs interfere with the normal function of the mRNA and these methods can be used to treat diseases, particularly HIV.

In the context of this invention, the term oligonucleotide refers to a plurality of joined nucleotide units formed from naturally-occurring bases and cyclofuranosyl groups joined by native phosphodiester bonds. This term effectively refers to naturally-occurring species or synthetic species formed from naturally-occurring subunits.

"Oligonucleotide analog," as that term is used in connection with this invention, refers to moieties which function similarly to oligonucleotides but which have non naturally-occurring portions. Thus, oligonucleotide analogs may have altered sugar moieties or inter-sugar linkages. Exemplary among these are the phosphorothioate and other sulfur containing species which are known for use in the art. They may also comprise altered base units or other modifications consistent with the spirit of this invention.

In accordance with certain preferred embodiments, at least some of the phosphodiester bonds of the oligonucleotide have been substituted with a structure which functions to enhance the ability of the compositions to penetrate into the region of cells where the RNA whose activity is to be modulated is located. It is preferred that such linkages be sulfur-containing. It is presently preferred that such substitutions comprise phosphorothioate bonds. Others such as alkyl phosphothioate bonds, N-alkyl phosphoramidates, phosphorodithioates, alkyl phosphonates, and short chain alkyl or cycloalkyl structures may also be useful. In accordance with other preferred embodiments, the phosphodiester bonds are substituted with structures which are, at once, substantially non-ionic and non-chiral. Persons of ordinary skill in the art will be able to select other linkages for use in the practice of the invention.

It is generally preferred for use in some embodiments of this invention that the 2' position of the linking sugar moieties in at least some of the subunits of the oligonucleotides or oligonucleotide analogs be substituted. Thus, 2' substituents such as OH, SH, F, $OCH_3$, OCN, $OCH_nCH_3$: where n is from 1 to about 20 and other substituents having similar properties may be useful in some embodiments.

Oligonucleotide analogs may also include species which include at least some modified base forms. Thus, purines and pyrimidines other than those normally found in nature may be so employed. Similarly, modifications on the cyclofuranose portions of the nucleotide subunits may also occur as long as the essential tenets of this invention are adhered to.

Such analogs are best described as being functionally interchangeable with natural oligonucleotides (or synthesized oligonucleotides along natural lines), but which have one or more differences from natural structure. All such analogs are comprehended by this invention so long as they function effectively to bind to selected portions of tat RNA.

The oligonucleotides and oligonucleotide analogs in accordance with this invention preferably comprise from about 3 to about 100 subunits. It is preferred that such oligonucleotides and analogs comprise at least about 6 subunits with from about 8 to about 50 subunits being more preferred, and still more preferred to have from about 10 to about 20 subunits. As will be appreciated, a subunit is a base and sugar combination suitably bound to adjacent subunits through phosphodiester or other bonds.

The oligonucleotides and oligonucleotide analogs of this invention can be used in diagnostics, therapeutics and as research reagents and kits. For therapeutic use, the oligonucleotide or oligonucleotide analog is administered to an animal, especially a human, such as are suffering from a virus or retrovirus infection such as AIDS.

It is generally preferred to apply the therapeutic agents in accordance with this invention internally such as orally, intravenously or intramuscularly. Other forms of administration, such as transdermally, topically or intralesionally may also be useful. Inclusion in suppositories may also be useful. Use of the oligonucleotides and oligonucleotide analogs of this invention in prophylaxis is also likely to be useful. Use of pharmacologically acceptable carriers is also preferred for some embodiments.

In accordance with the present invention, it will be understood that the term "to bind" as it refers to the interaction between an oligonucleotide or oligonucleotide analog and an RNA portion or subportion may have any of several, related meanings. Thus, the present invention comprehends binding of an oligonucleotide or analog with at least one portion of tat RNA. It will be understood that the oligonucleotide or analog will bind with at least one portion of the RNA portion in a Watson-Crick fashion so as to form, locally, a heteroduplex between the RNA portion and the oligonucleotide or analog. This heteroduplex formation is believed to result in alteration of the structure or function of the RNA portion. The exact mechanism and the result of this effect is not known with certainty, yet it is believed that the normal structure or function of the RNA portion is gradually replaced by the binding of the oligonucleotide with one or more portions of the RNA. Since the electronic and steric factors which attend the new heteroduplex are different from those of the natural-occurring RNA portion, the effectiveness and nature of the function to generate protein from the RNA is interfered with. The resulting formation of defective or missing protein manifests itself overall as a modulation in the expression of the gene coding for the RNA.

In short, any interaction or binding of oligonucleotide or oligonucleotide analog with tat RNA is believed to have the potential for interference with RNA function and, hence, for modulation the expression of the gene from which the RNA derives. Tat RNA targets have been found which exhibit overall diminution of activity of HIV when oligonucleotides or oligonucleotide analogs corresponding to portions of the target are administered to infected cells.

While a wide variety of oligonucleotides and oligonucleotide analogs are believed to be useful in practice of the present invention, it has been found to be preferred to design such oligonucleotides and analogs so as to bind with at least about six subunits of a portion of RNA. In accordance with other preferred embodiments, oligonucleotides which combine with from about six to about 30 and even more preferably with about 10 to about 20 subunits are preferred. As discussed above, it is presently believed that the tat RNA of HIV comprises an excellent target for employment of the present invention. Accordingly, preparation of oligonucleotide or oligonucleotide analog for binding with one or more portions of the tat RNA region of HIV are preferred.

Therapeutics are particular objects of the present invention. Thus, presenting oligonucleotides and oligonucleotide analogs in accordance with the present invention in pharmaceutically acceptable carriers may be highly useful. This is especially true for treatment of the disease AIDS.

Overall, it is preferred to administer to patients suspected of suffering from the foregoing disease states with amounts of oligonucleotide or analog, in either native form or suspended in a carrier medium in amounts and upon treatment schedules which are effective to reduce the symptomology of that disease. It is within the scale of a person's skill in the art to determine optimum dosages and treatment schedules for such treatment regimens.

An elaborate set of control elements in the HIV genome determine whether the virus replicates or remains dormant. Of the nine genes identified in the HIV genome, only three are from the core and envelope. W. A. Haseltine, F. Wong-Staal, *Scientific American* Oct., 52 (1988). The other six genes are involved in regulation of the production of viral proteins. Regulatory genes work by encoding a protein that interacts with a responsive element somewhere else on the viral genome. The major regulatory gene responsible for initiating the burst of replication is the tat (transactivator) gene. FIGS. 1A and 1B is a sequence for the cDNA of the tat region in HIV. The product of the tat gene, tat protein, works by interaction with a short sequence element known as TAR (trans-acting responsive element). The TAR sequence is encoded in the viral long terminal repeats (LTR's), and therefore is included in the mRNA from every HIV gene.

Expression of the tat protein results in increased expression of other HIV genes up to 1,000 fold, including the tat gene itself. Because of this autoregulatory positive feedback, and the fact that the TAR sequence in included in the mRNA from every HIV transcript, a immense amount of viral gene expression is triggered when the tat gene is activated. The interaction between the tat gene and the TAR element is therefore crucial to the life cycle of the HIV, and specific disruption of this interaction is likely to interrupt the propagation of the virus.

The mechanism of trans-activation of TAR-containing genes by the tat protein has recently been studied intensely. Philip,A. Sharp, Robert,A. Marciniak, Cell 59, 229 (1989). Although much remains to be learned, two important points have become clear; that tat increases the expression of TAR-containing genes by increasing both the amount of viral mRNA and the efficiency of its translation, and that TAR functions as an RNA structure, rather than a DNA structure.

The unusual conclusion that tat increases the transcription of TAR-containing genes, but does so by interacting with the TAR element in RNA was derived from a number of observations. Philip,A. Sharp, Robert,A. Marciniak, *Cell* 59, 229 (1989). In order to achieve trans-activation, the TAR element must be located immediately downstream from the site of initiation of transcription. Moreover, TAR is orientation dependent; if inserted in the inverse orientation, it fails to function.

Some of the strongest evidence that tat interacts with TAR as an RNA structure has come from mutagenesis experiments. Efforts to study the TAR element were stimulated by the observation that the tat protein from HIV-1 was capable of trans-activating vectors containing the TAR region of HIV-2, a different strain of virus, even though there is very little primary sequence homology in the TAR region between the two strains. S. Feng, E. C. Holland, *Nature* 334, 165 (1988). However, examination of the TAR sequence from HIV-1 and HIV-2 with computer programs that predict RNA secondary revealed the potential of RNA stem-loop structures, with a single stemloop in the TAR region of HIV-1 and three stem-loop structures in HIV-2. Although the compositions and lengths of the stems were divergent, all four loops contained the pentanucleotide CUGGG as shown in FIGS. 1A and 1B. Mutagenesis experiments revealed that each of the nucleotides present in the loop are absolutely essential for trans-activation by tat, but that base substitutions in the stem were tolerated to some extent so long as the stem *structure* was maintained. S. Feng, E. C. Holland, *Nature* 334, 165 (1988).

Further evidence for the TAR structure functioning as RNA was obtained from experiments in which the sequences flanking the stem-loop structure were altered creating competing secondary structures in the RNA that were more stable than the natural TAR stem-loop. B. Berkhout, *Cell* 59, 273 (1989). This was accomplished by introducing additional sequences into the TAR-containing RNA that were antisense to the 5' side of the stem-loop structure. Trans-activation of the modified TAR structure was lost, suggesting that the TAR sequences alone are not sufficient for trans-activation, but that these sequences must fold up in the proper secondary structure to be active. It also suggests that antisense sequences to the TAR stem-loop are capable of disrupting the natural RNA structure.

Direct biochemical evidence for TAR stem-loop structure has also been obtained. The TAR RNA has been enzymatically synthesized in vitro and probed with enzymes selectively cleave single stranded regions of RNA, but not duplex structures. The results of the enzyme cleavage patterns were consistent with the computer predicted RNA secondary structure. B. Berkhout, *Cell* 59, 273 (1989).

In summary, there is strong and direct evidence from a number of studies that the HIV tat protein is responsible for triggering an enormous amount of viral gene expression, that this occurs by interaction with the TAR sequence which is incorporated into every HIV mRNA transcript, that the HIV TAR sequence functions as an RNA structure and that the correct TAR RNA structure is essential for tat transactivation.

TAR and tat function has been studied by removing the genes from the HIV genome and studying them in cell lines in isolation. Vectors have been constructed to study the interactions between the tat protein and TAR element. The tat gene is expressed under the SV40 promoter. The TAR region is expressed from a separate plasmid fused to an easily assayed reporter gene, the placental alkaline phosphatase gene (PAP). P. Henthorn, P. Zervos, M. Raducha, H. Harris, T. Kadesch, *Proc. Natl. Acad. Sci. USA* 85, 6342 (1988) Enzymatic activity in cell culture models has been shown to be dependent upon both the presence of the essential elements of the TAR region and the presence of the tat protein. P. Sharp, R. Marciniak, *Cell* 59, 229 (1989); S.

Feng, E. C. Holland, *Nature* 334, 165 (1988); Michael,F. Laspia, Andrew,P. Rice, Michael,B. Mathews, *Cell* 59, 283 (1989); J. A. Garcia, D. Harrich, E. Soultanakis, F. Wu, R. Mitsuyasu, R. B. Gaynor, *EMBO J.* 8, 765 (1989); and B. Berkhout, *Cell* 59, 273 (1989). In essence, the vector system reconstitutes the events of tat-mediated TAR transactivation in which occurs in HIV infected cells.

TAT/TAR trans activation can be conveniently assayed by placing the human placental alkaline phosphatase gene (PAP) under the regulatory control of the HIV-1 LTR sequences, which contain enhancer, promoter, and tar elements. A plasmid containing the HIV-1 LTR, pHIVCAT-0 (S. Feng, E. C. Holland, *Nature* 334, 165 (1988)), contains HIV U3 in its entirety and R up through position +78 (a HindIII site). Digestion of this plasmid with a combination of HindIII and AatII releases the CAT cassette along with the SV40 sequences responsible for the processing of the RNA. A second plasmid, pSV2Apap, contains the PAP cassette with eukaryotic processing signals, under the transcriptional control of an SV40 promoter. P. Henthorn, P. Zervos, M. Raducha, H. Harris, T. Kadesch, *Proc. Natl. Acad. Sci. USA* 85, 6342 (1988). The PAP cassette and processing sequences were released from the plasmid by digestion with HindIII and AatII. A new plasmid, pHIVPAP, was created by ligating the HindIII/AatII fragment containing the HIV-1 LTR and vector sequences from pHIVCAT-0, to the HindIII/AatII PAP cassette from pSV2Apap.

To test the activity of oligonucleotide analogs, pcDEBtat and pHIVPAP were co-transfected into HeLa cells by calcium/phosphate precipitation. The effects of the selected oligonucleotide analogs was determined as follows. HeLa cells were split 1:8 into 6-well dishes the day prior to the transfections. For each dish, lug of pHIVPAP and 12ug of pcDEBtat were precipitated in 500 μl of HBS and 32 μl of 2.5 M CaCl₂. The CaPO₄ precipitate was divided evenly between the 6 wells. Oligonucleotides or oligonucleotide analogs were precepitated in the same manner and added to the cells at the concentrations indicated in the figures. The precipitate was allowed to sit on the cells for 20 minutes then complete media was added and the cells were incubated for an additional 4 hours. The cells were then shocked with 10% glycerol in HBS.

After 48 hours, cells were harvested and protein and PAP assays performed as described by Henthorn et al. P. Henthorn, P. Zervos, M. Raducha, H. Harris, T. Kadesch, *Proc. Natl. Acad. Sci. USA* 85, 6342 (1988) with the following modifications. The cells were harvested in 0.5 ml of TBS, of which 0.1 mls were used for use in the protein assay. The remaining 0.4 mls of cell suspension was pelleted then resuspended in 50 μl TBS. Endogenous phosphatases were inactivated by heating the cells at 65° C. for 30 min. The heat stable human placental alkaline phosphatase activity was assayed by the addition of PNPP (0.5 ml, 5 mM PNPP) to the cell suspension, which was then incubated at 37° C. Activity was determined at 30 minute intervals using 150 μl aliquots of the reaction mixture and measuring absorbance at 405 nm with a Titertek Multiscan MCC∖340 ELISA plate reader. The PAP activity was normalized total protein in each well as determined by Bio-Rad protein assay, in which 1∖5 of the harvested cells in TBS(0.1 μl) were added to 30 of BioRad Protein Reagent, then incubated for 10 minutes at room temperature, followed by measurement of absorbance at 595 nm using the Titertek plate reader.

Cells were treated with the following oligonucleotide analogs having phosphorothioate backbones:

| # | 5' | 3' |
|---|---|---|
| 461 | GGCTCCATTTCTTGCTCTCC | |
| 462 | CATTTCTTGCTCTCCTCTGT | |
| 463 | GCTATGTCGACACCCAATTC | |
| 464 | CCGCCCCTCGCCTCTTGCCG | |
| 465 | CGGGTCCCCTCGGGATTGGG | |
| 466 | CACCTTCTTCTTCTATTCCT | |
| Control | TGGCATCGAT GCTCA | . |

The data are displayed graphically in FIG. 2. Significant diminution in PAP activity, which is a direct measure of gene expression from the HIV LTR, was exhibited by the phosphorothioate oligonucleotide analogs bearing code numbers 461, 462, 463, 464 and 465. Oligonucleotide 466 and the control oligonucleotide, which was not designed to be complementary to the tat mRNA did not exhibit significant activities in this assay. The apparent increase in PAP activity at the 1 uM dose for the control oligonucleotide and compound number 466 probably resulted from a carrier effect in which the oligonucleotides facilitated uptake of the plasmids at the time of transfection. This effect may have been present in experiments with the active oligonucleotides, but was masked by the specific inhibitory activities of these compounds.

What is claimed is:

1. An oligonucleotide analog with a phosphorothioate backbone having a nucleotide sequence selected from the group consisting of:

5'                              3'

GGCTCCATTTCTTGCTCTCC

CATTTCTTGCTCTCCTCTGT

GCTATGTCGACACCCAATTC

CCGCCCCTCGCCTCTTGCCG

CGGGTCCCCTCGGGATTGGG

CACCTTCTTCTTCTATTCCT .

2. A pharmaceutical composition comprising the oligonucleotide analog of claim 1 in a pharmaceutically acceptable carrier.

* * * * *